(12) United States Patent
Chautems et al.

(10) Patent No.: US 11,521,307 B2
(45) Date of Patent: Dec. 6, 2022

(54) METHOD AND SYSTEM FOR PROPELLING AND CONTROLLING DISPLACEMENT OF A MICROROBOT IN A SPACE HAVING A WALL

(71) Applicant: ETH ZÜRICH, Zürich (CH)

(72) Inventors: Christophe Chautems, Zürich (CH); Bradley James Nelson, Zumikon (CH)

(73) Assignee: ETH ZÜRICH, Zürich (CH)

(*) Notice: Subject to any disclaimer, the term of this patent is extended or adjusted under 35 U.S.C. 154(b) by 422 days.

(21) Appl. No.: 16/715,260

(22) Filed: Dec. 16, 2019

(65) Prior Publication Data
US 2020/0193586 A1   Jun. 18, 2020

(30) Foreign Application Priority Data
Dec. 17, 2018   (EP) ..................... 18213092

(51) Int. Cl.
*G06T 7/00* (2017.01)
*G05D 1/02* (2020.01)

(52) U.S. Cl.
CPC ......... *G06T 7/0002* (2013.01); *G05D 1/0212* (2013.01); *G06T 2207/10088* (2013.01)

(58) Field of Classification Search
CPC ......... G06T 7/0002; G06T 2207/10088; A61B 34/73; A61B 34/72; A61B 2034/107;
(Continued)

(56) References Cited

U.S. PATENT DOCUMENTS 7,962,194 B2   6/2011   Martel et al.
8,830,648 B2   9/2014   Abbott et al.
(Continued)

FOREIGN PATENT DOCUMENTS

DE   10 2010 022 926 A1   12/2011
DE   10 2011 006 948 A1   10/2012
(Continued)

OTHER PUBLICATIONS

Nelson et al.; "Microrobots for Minimally Invasive Medicine;" Annual Review of Biomedical Engineering; 2010; pp. 55-85; vol. 12, No. 1.
(Continued)

*Primary Examiner* — Brenda C Bernardi
(74) *Attorney, Agent, or Firm* — Oliff PLC

(57) ABSTRACT

A method and system for propelling and controlling displacement of a microrobot in a space having a wall, includes the steps of: forming the microrobot with a body containing a magnetic field-of-force responsive material, wherein, in response to a magnetic field of force, a force is applied to the material in a direction of the magnetic field of force; positioning the microrobot in the space for displacement in that space; and generating the magnetic field of force with a predetermined gradient and applying the magnetic field of force to the microrobot propelling the microrobot through the space in a direction of a field of force. Then, a sequence of field generating steps are executed, wherein each step includes calculating the direction, amplitude and spatial variation of the net field of force to control displacement of the microrobot in the space and against the wall from one equilibrium point to another.

17 Claims, 7 Drawing Sheets

FIG. 5

(58) Field of Classification Search
CPC .... A61B 2018/00446; A61B 2090/374; A61B 2017/00004; A61B 2017/00876; A61B 2018/00404; A61B 2090/376; A61B 2017/00345; A61B 2034/105; G05D 1/0212

See application file for complete search history.

(56) References Cited

U.S. PATENT DOCUMENTS

| | | |
|---|---|---|
| 2004/0210128 A1 | 10/2004 | Martel et al. |
| 2011/0301452 A1 | 12/2011 | Maschke et al. |
| 2012/0281330 A1 | 11/2012 | Abbott et al. |
| 2013/0154776 A1* | 6/2013 | Mahoney ................ H01F 7/02 335/219 |
| 2016/0263391 A1* | 9/2016 | Tasci ...................... A61B 34/73 |
| 2018/0221041 A1* | 8/2018 | Creighton ............. A61M 37/00 |
| 2020/0100658 A1* | 4/2020 | Abbott ................ A61B 1/00156 |
| 2021/0052190 A1* | 2/2021 | Kiselyov ........... A61M 5/14276 |
| 2021/0052855 A1* | 2/2021 | Kiselyov ............... A61L 29/085 |
| 2021/0059779 A1* | 3/2021 | Zhao ................... A61B 34/20 |
| 2021/0401526 A1* | 12/2021 | Shpigelmacher .. A61K 49/0002 |

FOREIGN PATENT DOCUMENTS

| | | |
|---|---|---|
| EP | 2 475 322 B1 | 3/2016 |
| WO | 2011/029592 A1 | 3/2011 |

OTHER PUBLICATIONS

Martel; "Microrobotics in the vascular network: present status and next challenges;" Journal of Micro-Bio Robotics; 2013; pp. 41-52; vol. 8, No. 1.

Chautems et al.; "Magnetically powered microrobots: A medical revolution underway?" European Journal of Cardio-thoracic Surgery; 2017; pp. 405-407; vol. 51, No. 3.

Jun. 7, 2019 Search Report issued in European Patent Application No. 18213092.2.

* cited by examiner

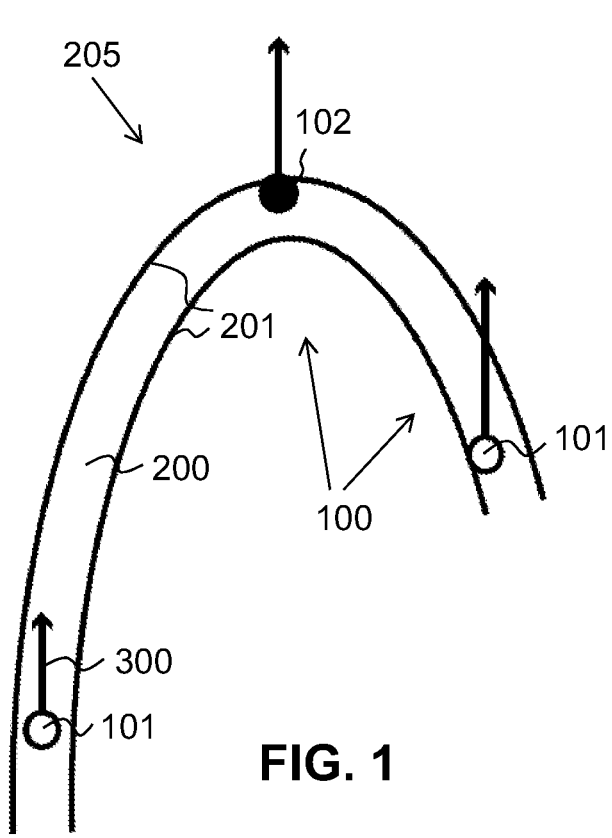
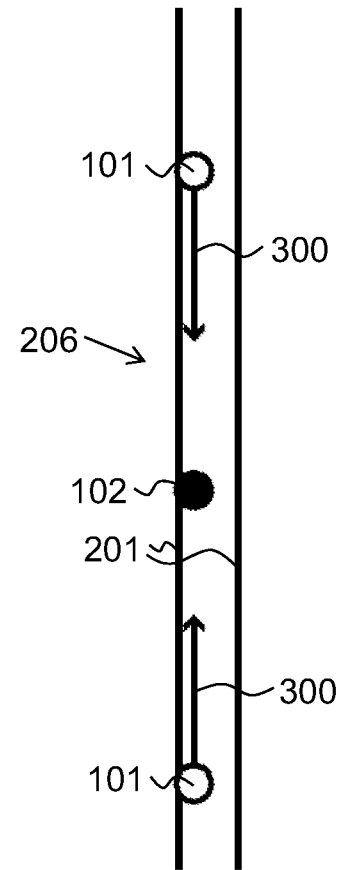
FIG. 1
FIG. 2
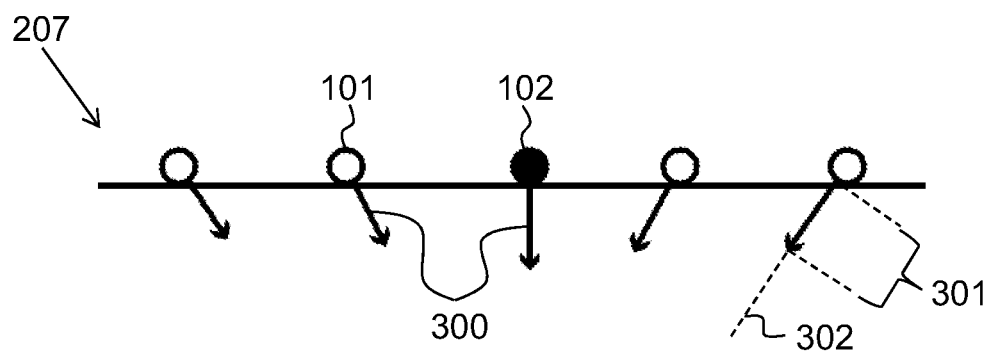
FIG. 3

METHOD AND SYSTEM FOR PROPELLING AND CONTROLLING DISPLACEMENT OF A MICROROBOT IN A SPACE HAVING A WALL

TECHNICAL FIELD

The present invention relates to a method and a microrobot system for propelling and controlling displacement of a microrobot in a space having a wall.

PRIOR ART

Microrobots are promising for targeted delivery of therapeutics to precise locations within the human body. However, the use of magnetic microrobots has been limited by the inability to navigate them in a large operating volume as mentioned by S. Martel in "Microrobotics in the vascular network: present status and next challenges," Journal of Micro-Bio Robotics, vol. 8, no. 1, pp. 41-52, 2 2013.

A popular way to actuate micro- or nanorobots is to wirelessly control them with a magnetic field as disclosed by B. J. Nelson, I. K. Kaliakatsos, and J. J. Abbott in "Microrobots for Minimally Invasive Medicine," Annual Review of Biomedical Engineering, vol. 12, no. 1, pp. 55-85, 7 2010.

Magnetic actuation can be achieved in a 3D fluidic environment using magnetic field gradient pulling, rotating magnetic fields and oscillating magnetic fields. Magnetic microrobots designed for micromanipulation on a 2D surface were propelled with an oscillating magnetic field to create a mechanical resonance and by rolling in a rotating magnetic field.

A microrobot system is described in US 2004/210 128 A1, showing a method and system intended to propel and control displacement of a microrobot through a patient's blood vessel. The microrobot is formed with a body containing field-of-force responsive material wherein, in response to a field of force, the material undergoes a force in the direction of the field of force. The microrobot is designed to be positioned in a blood vessel for displacement through the blood vessel, and a field of force is generated and applied to the microrobot in view of propelling the microrobot through the blood vessel in the direction of the field of force. A direction and amplitude of the field of force is calculated to thereby control displacement of the microrobot through the patient's blood vessel. A Mill system is suggested to generate a magnetic field gradient and to track the displacement of the microrobot, which can be used as a position feedback. Tests were made using water instead of blood in a plastic (PMMA) tube into which water is pumped to generate a water flow regulated by a flow meter. The microrobot is formed as a ferromagnetic sphere in the form of a carbon steel ball of 3.175 mm and is placed in the tube. A magnetic gradient is applied to the microrobot to generate a magnetic force to counter the drag forces experienced by the microrobot due to the water flow. During the test, the valve of the flow meter is adjusted until the drag force exerted on the microrobot is countered by the magnetic force and the microrobot reaches a position in the tube which is referred to as an equilibrium position in the water flow. A microrobot system allowing the navigation of a magnetic robot from an equilibrium point to another equilibrium, in particular on the wall of the space in which the microrobot is moved, here the tube, is not disclosed.

Further, DE 10 2010 022 926 A1, also published as US 2011/301 452 A1, discloses a method for positioning a spatial region of a magnetic gradient field in which the holding forces produced are maximum, known as the focal point, at a target location, namely a tumor. To position the focal point of the gradient field at the target location, a catheter with at least one electromagnetic position sensor comprising at least one coil is guided to the target location subject to image monitoring, and the focal point is moved to the target location taking into account the signal measured from the position sensor. The positioning of the gradient field relative to the target location is then changed by relative displacement of the target location with the tumor and the gradient field until the signal from the position sensor indicates that the focal point and the target location correspond. This allows magnetic nanoparticles, and therefore also in particular microcapsules containing such magnetic nanoparticles, to be concentrated locally in an optimum manner at the target location. In one embodiment, provision can also be made for a catheter configured to inject the microcapsules containing the magnetic nanoparticles to be used. The catheter is then moved to the target location and serves there by means of the position sensor not only to position the gradient field but at the same time also to inject the microcapsules. Consequently, DE 10 2010 022 926 A1 discloses a process in which, in a first step, the focus of the gradient field is positioned relative to the target location in a sequence of steps and, in a second step when the focus of the gradient field corresponds to the target location, the microcapsules are injected for a displacement to the focus of the gradient field.

The navigation of a microrobot within a space having a wall, e.g. a lumen with curved portions and straight portions like the inner ear or a blood vessel of the vascular system, still needs to be improved, especially in low viscosity liquids like blood, because the displacement of the microrobot lacks precision and the positions, for example the equilibrium positions of the microrobot are instable due among other to the low damping capacity of low viscosity liquids.

SUMMARY OF THE INVENTION

It is an object of the present invention to provide an improved method and an improved microrobot system for navigating, i.e. for propelling and controlling a microrobot, especially in a constrained 3D volume in the form of a space having a wall, such as the brain vascular system or the inner ear. The microrobot can be, at least intermittently, in contact against the wall in the space.

This object is achieved through providing a sequence of field generating steps, executed one after the other, wherein each field generating step comprises calculating a direction, amplitude, and spatial variation of the field of force to control a displacement of the microrobot in the space and against said wall of the space from an equilibrium point to another equilibrium point.

The object is therefore achieved by providing a microrobot system comprising a magnetic field of force generator designed to generate a magnetic field of force with a predetermined direction, amplitude and spatial variation for application to the microrobot to propel the microrobot through the space.

Preferably the magnetic field of force generator is in the form of a magnetic navigation system with multiple electromagnets providing an inhomogeneous magnetic field at predetermined positions in the space, in which the microrobot comprised in the microrobot system is moved. Electromagnets are preferably used because of their flexibility and ease of use to control the magnetic field. The magnetic field can namely be changed by changing the electrical current inside the electromagnets and/or by moving the electromagnets, wherein the electromagnets are located around the patient. However, it is also possible to use permanent magnets located and movable around the patient or a combination of permanent and electromagnets.

The space in which the microrobot is moved can be mapped with an imaging system before the microrobot is introduced in the space or while the microrobot is in the space, either intermittently or continuously. When the space, in which the microrobot is moved, is mapped beforehand in relationship to the outside body, i.e. the outside of the space, no further imaging system is necessary to navigate the microrobot. This method is better adapted to create an high resolution map. On the other side an x-ray system can achieve a live microrobot control in the space like the brain vascular system or the inner ear. This method is better adapted when the space has a complex structure or a structure that can evolve over time. The use of an high resolution map acquired before the introduction of the microrobot can be combined with live x-tracking to exploit the advantage of both imaging methods.

Said inhomogeneous magnetic gradient of the magnetic field generated by the plurality of electromagnets is trapping the microrobot at specific locations along a lumen. The invention is based on the insight that a magnetic gradient inhomogeneity achieves a step-by-step movement for navigating in constrained volumes from one specific location to another specific location, i.e. from an equilibrium point to the next equilibrium point.

Internal surfaces are used with magnetic fields and field gradients so that a control unit which is comprised in the microrobot system determines possible stable positions, and the microrobot is then moved through manipulation of the magnetic field between these previously determined stable configurations. To navigate between these stable discrete positions, the invention relies on the position dependence of the magnetic field gradient to allow the control unit to calculate a position with a local force equilibrium. These local minima of energy corresponding to equilibrium positions of the microrobot are the result of spatial variations in the magnetic gradient along the microrobot's unconstrained direction of motion. Changes in the magnetic field gradient, and, hence, the direction of the magnetic force, traps the microrobot at specific locations.

It is preferred to use preoperative imaging to create in advance a 3D-map, preplan the navigation path, and execute the path without continuous microrobot position feedback. Along this predetermined path the microrobot can be navigated and monitored in a large workspace using a human scale magnetic navigation system integrated with an x-ray system.

Soft magnetic or hard magnetic microrobot can be used. A soft magnetic microrobot is composed of material which get magnetized in the presence of a magnetic field and does not maintain its magnetization in the absence of a magnetic field. Hard magnetic microrobots are composed of material that retains their magnetization.

Using magnetic gradient inhomogeneity allows navigating the microrobot in a lumen filled with a low viscosity liquid without high frequency position feedback and control. The features of this method allow operating a microrobot inside the human body. It can now navigate in a large workspace and it can navigate against a liquid flow, i.e. the blood flow inside a human body.

In other words, a microrobot system is suggested which is composed of a plurality of magnets, preferably electromagnets to create a position dependent magnetic force on a magnetic element in the form of a microrobot inside a three-dimensional geometry. Preferably, the three-dimensional geometry forming the space is delimited by surfaces extracted from preoperative imaging. The system is capable to create a stable equilibrium position at one specific location on the surface or wall of the space by controlling the magnetic force to have the sum of all forces parallel to a plan approximating the wall of the space at the specific location cancelling and the normal force being cancelled by the surface contact force. At the equilibrium point the sum of all forces parallel to the plan tangent to the equilibrium point are cancelled and the normal force applied at this point on the microrobot is cancelled by the surface contact force. The controller further calculates different electromagnet currents for the magnetic navigation system to move this stable equilibrium location along the surfaces delimiting the three-dimensional geometry to move the magnetic element on the surface.

Without friction of the microrobot with the wall, the equilibrium point can be a single point. However, the microrobot is submitted to friction in a practical case and the equilibrium point must be understood as an equilibrium region in which the microrobot is in a stable position. In case of small disturbances corresponding to small offsets from the equilibrium point, the net forces acting on the microrobot are too low to overcome the friction and the microrobot remains in the equilibrium region or converge toward the equilibrium region.

Within the microrobot system as defined above, the two-dimensional surfaces can be a "lumen" and the sum of all forces is cancelled at a location along the longitudinal axis of the lumen. Then a stable equilibrium is created at a longitudinal position by having the net axial force pushing the magnetic element toward the stable equilibrium if there is a longitudinal position offset caused e.g. by disturbances.

Within the method according to an embodiment of the invention, the equilibrium points can be chosen to be at the wall of the space.

As a result, the navigation of the microrobot within the space can be significantly improved, especially in low viscosity liquids like blood, because the displacement of the microrobot is realized from an equilibrium position to another equilibrium position on the wall. Indeed, the interaction between the wall and the microrobot creates equilibrium position which are more stable than those in the space, i.e. not in contact with the wall, the latter being strongly dependent on the damping capacity of the liquids.

In a preferred embodiment the control unit is designed to execute the field generating steps at a frequency ranging from 0.2 Hz to 1000 Hz, preferably from 0.5 Hz to 100 Hz. The latter range has the advantage that the microrobot can be stabilized in the equilibrium position against the wall before the next field generating step is executed. More preferably, the frequency ranges from 1 Hz to 10 Hz to reach an optimal stabilisation of the microrobot against the wall.

Furthermore, in a preferred embodiment, the next field generating step can already be engaged, i.e. the control unit triggers the magnetic field of force generator to generate the next magnetic field of force, when the next equilibrium point is reached, so that there is only a short stop or no real stop at all at the equilibrium points. Concretely, the duration of the stop is limited by the frequency at which the field generating steps are executed and the time needed to cover the distance between two consecutive displacements of the microrobot.

In a preferred embodiment, the next field generating step is engaged at a time before the microrobot has reached the next equilibrium and calculated such that the microrobot at least approximately does not stop at the equilibrium position. This configuration has the advantage that the motion of the microrobot is essentially continuous in the space and along the wall so that it can be easily controlled.

Providing a direction, amplitude, and spatial variation of the field of force to control the displacement of the microrobot can comprise, for a predetermined number of all field generating steps of the sequence, especially for all field generating steps, the step of calculating said direction, said amplitude, and said spatial variation of the field of force prior to any of said predetermined number of all field generating steps.

On the other side, providing a direction, amplitude, and spatial variation of the field of force to control the displacement of the microrobot for a specific field generating step can comprise calculating said direction, said amplitude, and said spatial variation of the field of force at the beginning of said field generating step. This allows checking the position of the microrobot, i.e. if he is at the intended place, via a second visualization channel.

The microrobot system according to an embodiment of the invention comprises the microrobot for displacement through the space having the wall, especially a lumen, the microrobot being formed with a body containing a field-of-force responsive material, preferably a magnetic field of force responsive material, more preferably a magnetic material, wherein, in response to a field of force, especially a magnetic field of force, a force is applied to the material in a direction of the magnetic field of force.

The magnetic field of force generator generates the magnetic field of force with a predetermined direction, amplitude and spatial variation for application to the microrobot to propel the microrobot through the space or lumen in the direction of the field of force.

Moreover, the microrobot system comprises a control unit connected to the field of force generator calculating based on the direction, the amplitude, and the spatial variation of the field of force the displacement of the microrobot through the space. The direction of displacement of the microrobot depends on a net field of force which is the sum of all the forces acting on the microrobot, including e.g. the gravity field of force, the buoyancy force and additional forces acting on the microrobot. Therefore, the term field of force has to be understood as net field of force.

Concretely, the control unit is connected to the magnetic field of force generator and designed to calculate a direction, an amplitude, and a spatial variation of the net field of force acting on the microrobot. Further, the control unit is designed to control the displacement of the microrobot through the space and along the wall under the action of the net field of force and to calculate equilibrium points of the microrobot on the wall using data relating to the image of the space and the calculated direction, amplitude, and spatial variation of the net field of force.

Moreover, the control unit is designed to create a sequence of field generating steps, executed one after the other, wherein each field generating step comprises providing a direction, an amplitude and a spatial variation of the net field of force to control the displacement of the microrobot in the space and against the said wall of the space from an equilibrium point to another equilibrium point.

Concretely, the calculation to provide the direction, the amplitude and the spatial variation of the net field of force comprises calculating the direction, the amplitude and the spatial variation of the magnetic field of force, which data are transmitted to the magnetic field of force generator by the control unit, wherein the control unit triggers the magnetic field of force generator to generate the corresponding magnetic field of force.

The control unit can also be designed to calculate a change of the direction of the magnetic field in at least one field of force generating step and to trigger the magnetic field of force generator to change the direction of the magnetic field in at least one field of force generating step. As a result of the change of the direction of the magnetic field, the magnetic field vector is rotated and the resulting force acting on the microrobot creates a torque on the microrobot and consequently a rotation of the microrobot, which helps the microrobot to overcome friction or adhesive force to the wall.

In a preferred embodiment, the microrobot is at least approximately spherical. This form has the advantage that a blocking of the microrobot in the space and against the wall can be reduced.

The combination of the spherical form of the microrobot and the change in the direction of the magnetic field leads to an efficient rotation of the microrobot which helps to overcome friction or adhesive force to the wall and supports the rotation of the microrobot on the wall. This rotation dynamic is advantageous for a more precise displacement of the microrobot.

In a preferred embodiment, the direction of the magnetic field is changed in each field of force generating step. This rotation dynamic is advantageous for a more precise displacement of the microrobot over the whole displacement of the microrobot.

The invention also relates to a control unit for use in the microrobot system according to any one of the embodiments described above, wherein the control unit comprises a processor configured to carry out the steps of:

Obtaining data relating to the image of the space having a wall from an imaging system;

Determining a first position of the microrobot in the space, the microrobot being formed with a body containing a magnetic field of force responsive material, preferably a magnetic material, wherein a force is applied to the microrobot in response to a magnetic field of force in a direction of the magnetic field of force;

Calculating the direction, the amplitude, and the spatial variation of the net field of force applied on the microrobot corresponding to the direction, the amplitude, and the spatial variation of a magnetic field of force in the space;

Calculating the displacement of the microrobot through the space and along the wall, using the direction, amplitude, and spatial variation of the net field of force calculated and data relating to the image of the space, from the first position, which can be an equilibrium position on the wall, to a second position of the microrobot under the net field of force;

Repeating the calculation for different magnetic fields of force in the space corresponding to spatial variations of the magnetic field of force to find a magnetic field of force resulting in at least one second position which is an equilibrium position of the microrobot on the wall. Possible strategies to explore the spatial variation of the magnetic field of force are discussed below.

Further, the processor is configured to carry out the step of selecting the magnetic field of force corresponding to an equilibrium position of the microrobot on the wall which can be used as the second position.

A criterium or a combination of criteria can be used to determine the optimal motion, i.e. the optimal second position of equilibrium and the corresponding the magnetic field of force, namely
a) the distance to a target location;
b) the size of the equilibrium region, i.e. the surface around the position at which the microrobot will be at an equilibrium position;
c) the size of the attraction region;
d) the confidence on the model accuracy; and
e) the ability of the microrobot to overcome friction on the wall.

Moreover, the processor is configured to carry out the step of transferring the direction, the amplitude, and the spatial variation of the selected magnetic field of force in the space corresponding to the equilibrium point for the second position to a magnetic field of force generator for generating the magnetic field of force and propelling the microrobot through the space in the direction of the net field of force from the first position to the second position.

Concretely, the strategy to choose different magnetic fields of force in the space for which the calculation is repeated depends, among other parameters, on the geometry of the space and the number as well as position of the electromagnets with respect to the space.

For example, in the case of a field of force generator comprising eight electromagnets, the inhomogeneous force fields that can be generated are part of an eight-dimensional space which results in a large combination of electromagnet currents in the electromagnets to be explored.

This exploration of the spatial variation of the field of force can follow different strategies that can be implemented in the control unit and which can be used to select the different magnetic fields of force in the space for which the calculation is repeated. It is also possible to combine these strategies or apply them one after the other to reduce the number of different magnetic fields of force to be selected.

The following strategies can be used, namely
a) Canceling the force at one location on the wall or, in the case of a space having the form of a lumen, on the lumen central axis and sweeping over the resulting null space. This method is particularly suitable for moving precisely along a straight lumen by reducing friction.
b) Actively setting the force resulting toward the wall at a target location and sweeping over the resulting null space. This method is particularly suitable to move along a lumen on a specific side or to a precise location on a concave surface.
c) Rotating the magnetic field and adapt the point of control of the gradient. This method is particularly suitable for small motions.
d) Moving toward a target location by setting the force in the direction of the target position. particularly suitable for fast motion or for overcoming flow.
e) Small delta, i.e. variations, from the previous current. This method is particularly suitable to limit the require change of currents.
f) Small delta in the magnetic field.
g) Small delta of the electromagnet currents.
h) Non-directed strategy by evaluating random variation of the magnetic field.
i) Non-directed strategy by evaluating random variation of the currents.

In a preferred embodiment, the processor can be configured to include in the step repeating the calculation for different magnetic fields of force in the space the step of calculating the change of direction of the magnetic field necessary to create the torque applying on the microrobot and resulting in the rotation of the microrobot. Preferably, the change of direction of the magnetic field occurs when the microrobot is at the equilibrium position, so that the friction between the microrobot and the wall can be easily overcome. It is also possible to change the direction of the magnetic field before the microrobot reaches the equilibrium position, so that the friction between the microrobot and the wall can be reduced when the microrobot reaches the equilibrium position. This configuration can be used when the microrobot needs to be moved from the equilibrium position it has just reached to another equilibrium position with reduced friction, for example to reduce the time the microrobot remains at the equilibrium position and consequently to obtain a motion closer to a continuous motion.

In a preferred embodiment, the processor can be configured to model the rotation dynamic of the microrobot under the effect of a change of direction of the magnetic field and include the corresponding rotation dynamic of the microrobot, when calculating the displacement of the microrobot through the space and along the wall, using the direction, amplitude, and spatial variation of the net field of force calculated and data relating to the image of the space from the first position to the second position of the microrobot on the wall under the net field of force.

The invention also relates to a computer program product comprising instructions which, when the program is executed by the processor of the control unit disclosed above, cause the processor to carry out the steps of:
Determining a first position of the microrobot in the space;
Calculating the direction, the amplitude, and the spatial variation of the net field of force applied on the microrobot corresponding to the direction, the amplitude, and the spatial variation of the magnetic field of force in the space;
Calculating the displacement of the microrobot through the space and against the wall, using the calculated direction, amplitude, and spatial variation of the net field of force and data relating to the image of the space, from the first position to a second position of the microrobot on the wall under the net field of force;
Repeating the calculation for different magnetic fields of force in the space;
Selecting the magnetic field of force corresponding to an equilibrium position of the microrobot on the wall which can be used as the second position; and
Transferring the direction, the amplitude, and the spatial variation of the selected magnetic field of force in the space corresponding to the equilibrium point for the second position to a magnetic field of force generator designed to generate the magnetic field of force, and propelling the microrobot through the space in the direction of the net field of force from the first position to the second position.

Further embodiments of the invention are laid down in the claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 shows a schematic cross section view of a curved lumen portion with positions of a microrobot at different starting points moved using a method according to an embodiment of the invention;

FIG. 2 shows a schematic cross section view of a straight lumen portion with positions of a microrobot at different starting points moved using the method as explained in connection with FIG. 1;

FIG. 3 shows a schematic view of a partly flat wall boundary portion with positions of a microrobot at different starting points moved using the method as explained in connection with FIG. 1;

DESCRIPTION OF PREFERRED EMBODIMENTS

Figure 4:
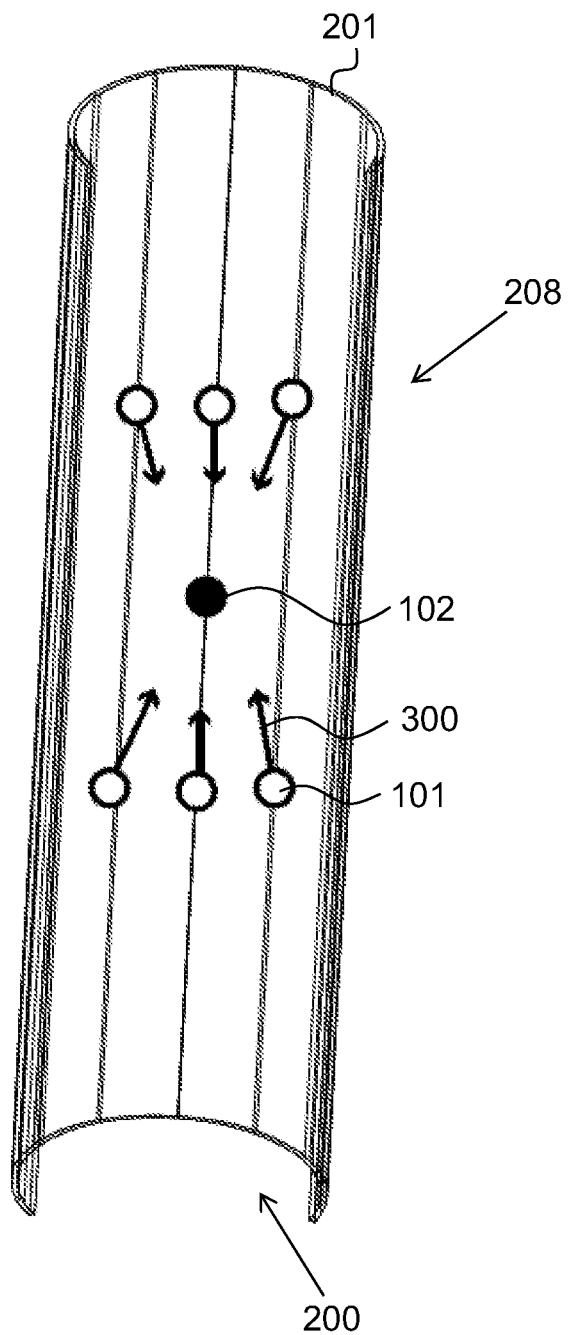
FIG. 4 shows a schematic view of a partly open straight lumen portion with positions of a microrobot at different starting points moved using the method as explained in connection with FIG. 1.

The method according to the embodiment as shown in FIG. 1 is based on the assumption that the microrobot is moved in a three-dimensional tubular geometry, i.e. a lumen, such as the brain vascular system or the inner ear cochlea.

FIG. 1 shows a schematic cross section view of a curved lumen portion 205 with positions of a microrobot 100 at different starting points 101 moved using a method according to an embodiment of the invention towards an equilibrium position 102.

This method is different to other methods to control microrobots floating without contact with a solid structure, since such methods usually use fluid with a high viscosity to dampen their motion.

To navigate a microrobot 100 within a space having a wall in the form of a blood vessel, e.g. a lumen with curved portions 205 and straight portions 206 as shown in FIG. 2 or partly open space with a wall 207 as in FIG. 3, as shown here, requires that the microrobot 100 is positioned in the space, i.e. introduced in the space in a position which can be an equilibrium position or an initial position from which the microrobot will move to a next equilibrium position, and controlled in a low viscosity liquid (3 cP to 4 cP).

The microrobot 100 is formed with a body containing a magnetic field of force responsive material in the form of a magnetic material. The body of the microrobot 100 can also contain other material and/or substance like therapeutics.

Figure 8:
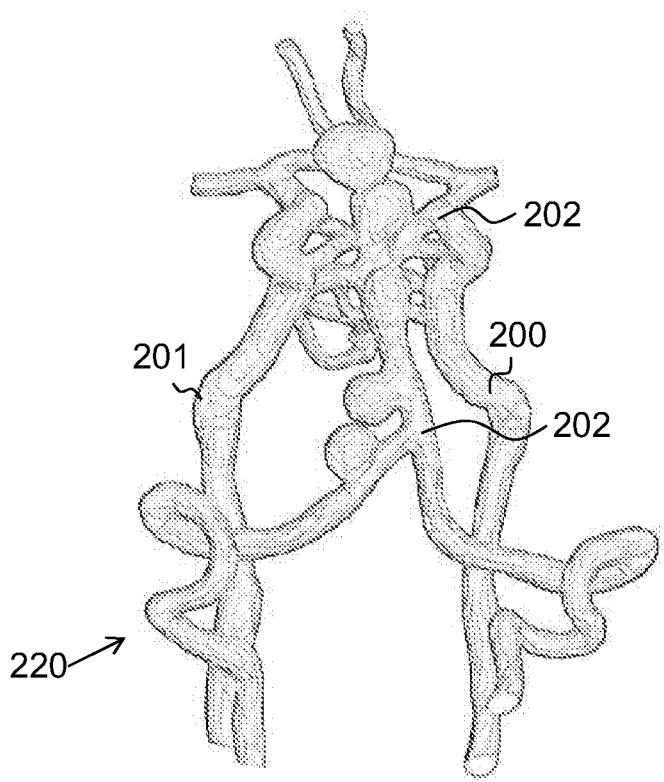
FIG. 8 shows a Circle of Willis, i.e. a circulatory anastomose in the brain, as example for a lumen having bifurcations.

Without damping, the microrobot 100 is rapidly pulled by the magnetic force and can easily exhibit unstable motion. However, an advantage of operating a microrobot 100 in the brain vascular system or cochlea is the absence of open space (in the sense that any portion of open space is limited by a wall 207) and the presence of tortuous paths as shown in FIG. 8.

The net force 300 is used to pull the microrobot 100 until it reaches a stable position 102 against the internal wall 201 of the lumen. By varying the direction 302, amplitude 301, and spatial variation of the force field, which can be a magnetic force field, the microrobot 100 moves between different stable positions 102 that can be predetermined within the network of the lumen. The direction of motion depends on the net field of force which is the sum of all the forces acting on the microrobot; these additional forces include e.g. the gravity field of force and additional forces acting on the microrobot. Therefore, the term field of force has to be understood as net field of force.

Here, stable positions 102 of the microrobot 100 are shown as full circles and non-stable positions 101 are shown as empty circles.

Figure 10:
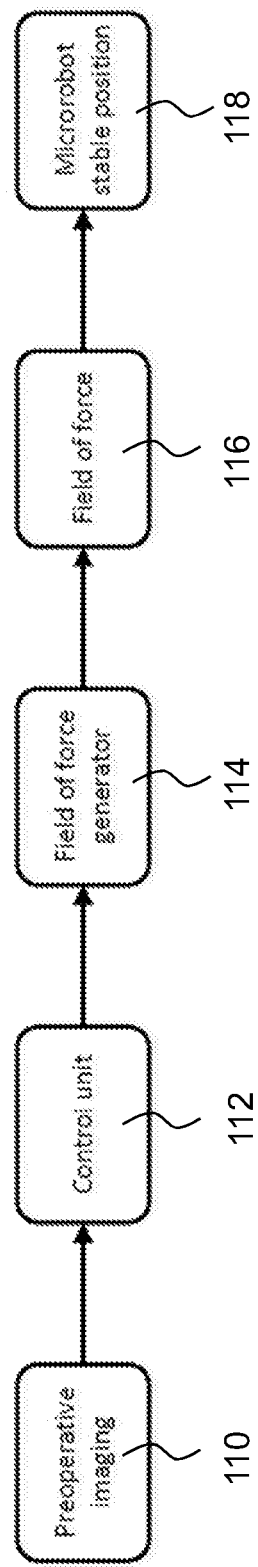
FIG. 10 shows a block diagram of a method to move a microrobot in a lumen according to FIG. 1.
Figure 11:
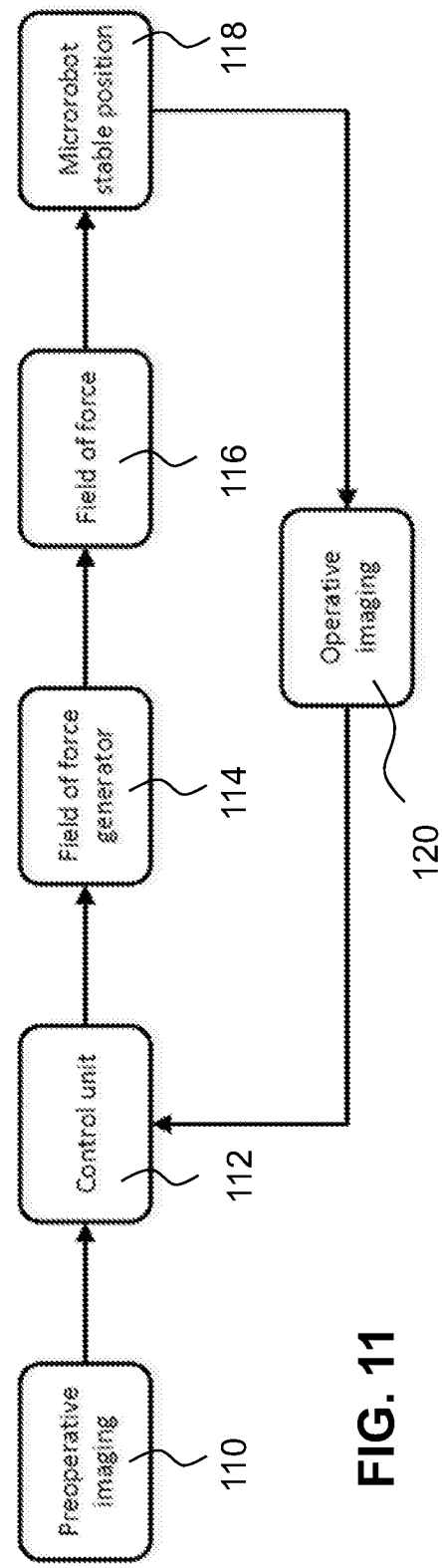
FIG. 11 show a block diagram similar to the method of FIG. 10 with operative imaging.

Predetermining stable positions within the method can be achieved in at least two ways. FIG. 10 shows a block diagram of a method to move a microrobot 100 in a space 200, especially a lumen with full prior knowledge of the environment where the microrobot 100 moves. A full prior determination is made, when the data relating to an image of the lumen is generated prior to the introduction of the microrobot 100, i.e. when the image of the lumen like in FIG. 8 is pregenerated by e.g. MRI or other imaging methods, so that the lumen portions 205, 206 and wall portions 201, 207 can be calculated in advance. This is shown as preoperative imaging 110. It is also possible to follow the microrobot 100 on the fly and generate the data image of the local environment where the microrobot 100 is moving in real-time, which is shown in FIG. 11.

Such a real-time monitoring as e.g. closed-loop control with fluoroscopy as feedback and operative imaging 120 which implies continuous irradiation of the patient, however, is not required. Such continuous feedback is not necessary using the present method using magnetic gradient inhomogeneity. X-ray images is only favorable to be acquired at the ends of motion sequences to confirm that the robot reached the desired target position.

To represent a lumen 205, the control unit 112 can be adapted and configured to use the centerline r(s) along the lumen axis with s parameterizing the displacement along the centerline. Motion is constrained along the radial direction by the lumen wall 201 or 207 and unconstrained along the axial direction $$\frac{\partial r(s)}{\partial s}.$$

To represent a complex structure such as the brain vascular system, each blood vessel segment 205, 206, 207 is represented by one centerline. The intersections at bifurcations 202 as shown in FIG. 8 between centerlines are stored in a connection graph that can be used for path planning. Centerlines can be extracted prior to microrobot navigation by processing preoperative imaging data obtained through preoperative imaging 110.

Microrobot propulsion can use a gradient pulling in which magnetic field gradients are generated by a magnetic resonance imaging machine (MRI) acting as a field of force generator 114. The gradient required to move a microrobot with a magnetic field gradient in the vascular system is quite high and magnetic gradients of 0.4 T/m were used to move microrobot against blood flow but especially steering them at arterial junctions.

An alternative to MM is to steer microrobots using a magnetic navigation system (MNS) designed for catheter steering as shown in C. Chautems, B. Zeydan, S. Charreyron, G. Chatzipirpiridis, S. Pané, and B. J. Nelson, "Magnetically powered microrobots: A medical revolution underway?" European Journal of Cardio-thoracic Surgery, vol. 51, no. 3, pp. 405-407, 2017. The magnetic gradient generated by a magnetic navigation system can be higher than for Mill, and an x-ray imaging system can be integrated for position feedback.

An integrated system of magnetic microrobots, a magnetic navigation system with multiple electromagnets, and an x-ray navigation system is an alternative to MRI with the potential to achieve microrobot control in the brain vascular system or the inner ear. It is possible to navigate a microrobot on the surface (=wall 205, 206, 207) of a three-dimensional volume, i.e. space 200, within an eight-electromagnet magnetic navigation system while exploiting magnetic gradient inhomogeneity to effect this microrobot actuation method.

Figure 6:
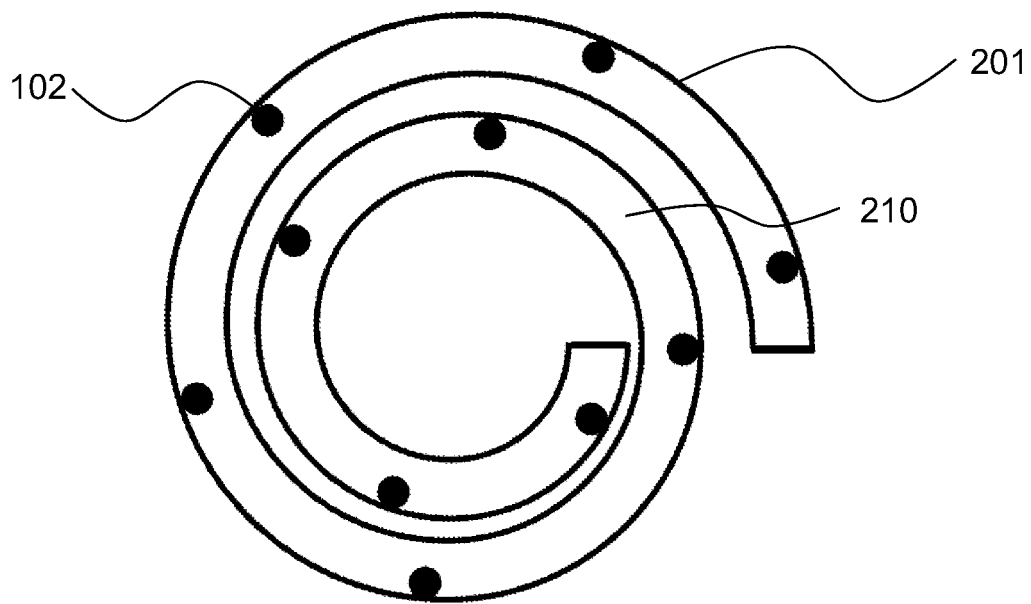
FIG. 6 shows a schematic view of a spiral lumen portion with ten positions of a microrobot at different equilibrium points moved using the method as explained in connection with FIG. 1.

A microrobot can be inserted via the round window and navigated inside the cochlea spiral for targeted delivery of a therapeutic. FIG. 6 shows in a schematic way like an x-ray image from a fluoroscopy system could monitor the microrobot 100, where all full black dots are showing a specific image of the microrobot 100 at various subsequently reached equilibrium positions 102 inside the spiral of the image.

In this context it can be referred again to FIG. 1 where a homogeneous magnetic force (since all arrows have equal length and identical direction), e.g. a field of force 116 generated by the field of force generator 114 controlled by the control unit 112 acting on data obtained by preoperative imaging 110, can pull the microrobot 100 toward a specific wall 201 portion, or a spatial variation of the magnetic force can create a stable equilibrium at one specific location as shown in FIG. 2 and FIG. 3, ending one movement step in a microrobot stable position 118.

FIG. 2 shows a schematic cross section view of a straight lumen portion 206 with positions of a microrobot 100 at different starting points 101 moving towards an equilibrium position 102 using the method as explained in connection with FIG. 1. FIG. 3 shows a schematic view of a partly flat wall boundary portion 207 with positions of a microrobot 100 at different starting points 101 moved using the method as explained in connection with FIG. 1—Here the directions 302 are converging below the wall portion 207 and finally the microrobot will move along the wall surface 107 towards the equilibrium position 102.

Figure 5:
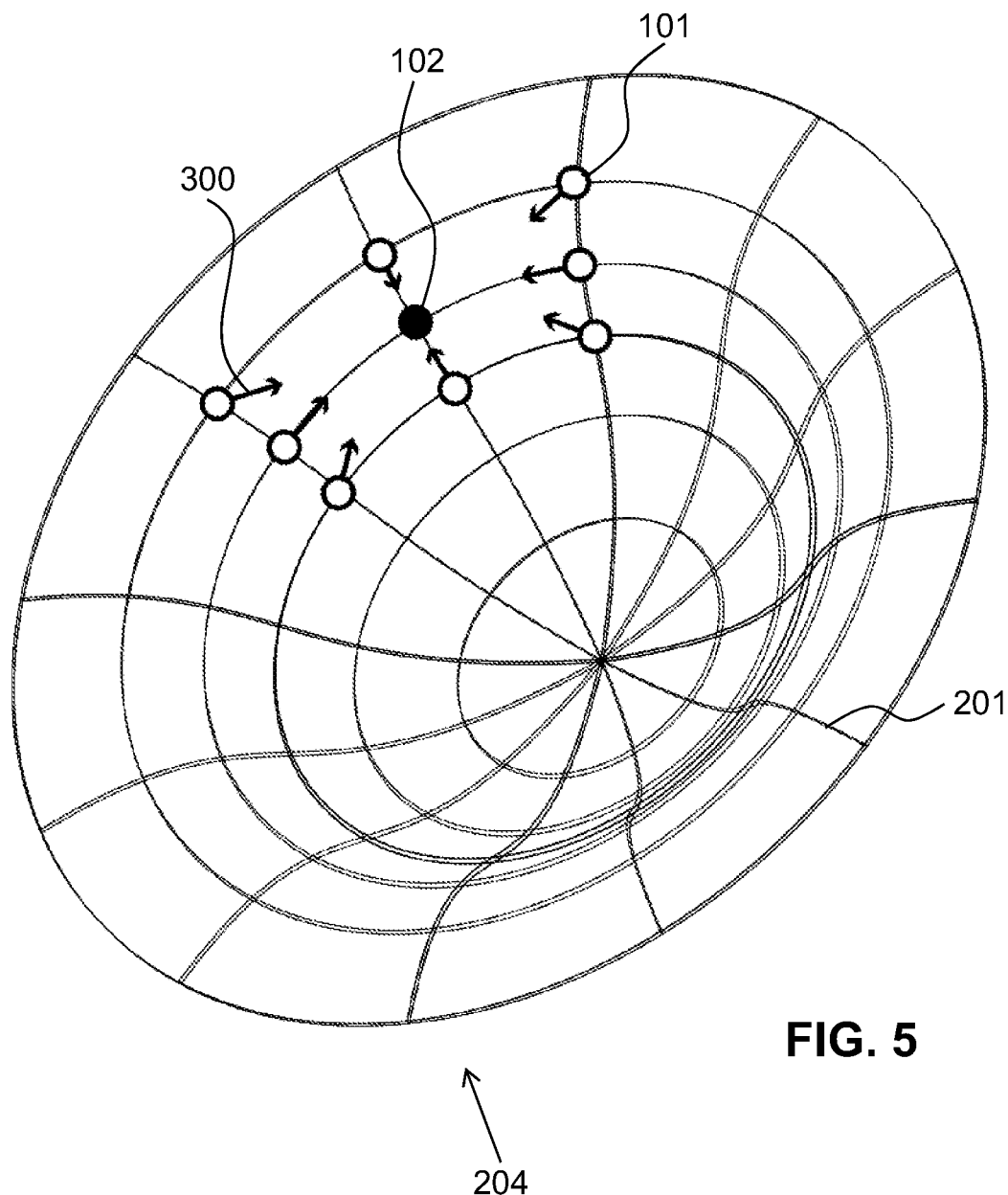
FIG. 5 shows a schematic view of a curved wall boundary portion with positions of a microrobot at different starting points moved using the method as explained in connection with FIG. 1.

Similar wall surfaces are shown in FIG. 4 for a side open sleeve and FIG. 5 for a dish-like side of an open space. Same reference numerals indicated identical or similar features throughout the specification.

The magnetic force imposes a constraint on microrobot size since the pulling force is dependent on both the magnetic volume and microrobot magnetization. Soft magnetic material can achieve higher magnetization but requires a non-zero magnetic field in order to be magnetized. In case of soft magnetic material, the microrobot will align with the magnetic field if he has a principal magnetization axis due to its shape, anisotropy in the material responsive to the magnetic field, or inhomogeneous distribution of the material responsive to the magnetic field. Some soft magnetic materials (e.g. FeCo/single-graphitic shell nanocrystals) have the advantage of being biocompatible. Iron-cobalt nanoparticles of diameter between 10 and 50 micrometer have been steered by an MM with additional gradient coils (0.4 T/m).

The magnetic force on small nanoparticles is too low to actuate them against the flow, and magnetic force is only used to steer them at a junction or bifurcation 202. An advantage of the present invention is that small nanoparticles can also be actuated if there is no flow or only a low flow in the space.

As opposed to Mill, a magnetic navigation system does not require a constant and uniform magnetic field direction. Therefore, in a magnetic navigation system, soft magnetic materials do not reach their saturation magnetization, which results in lower magnetic forces acting on the soft magnetic materials.

To operate with low magnetic fields requiring smaller electromagnets, microrobots made of a hard magnetic material (NdFeB) were chosen. These microrobots can be coated for biocompatibility but should be retrieved at the end of the procedure. The x-ray imaging resolution of 200 micrometer results in a constraint in terms of microrobot size (Ziehm Vision, Ziehm Imaging Inc.) of approximately 200 micrometer. A benefit of larger microrobots is that they require smaller magnetic gradients to swim against blood flow.

Magnetic force are used to control the net force to pull a microrobot 100 along a curved lumen 205. The forces acting on the microrobot 100, including gravitation force $F_{grav}$, buoyancy force $F_{buo}$, and drag force $F_{drag}(s)$, should be compensated by an opposing magnetic force. The buoyancy force and the gravitational force are constant along the path. The drag force acts opposite to the relative motion of the microrobot 100 and is oriented along the lumen axis in a constant diameter lumen. Turbulent flow and wall effects can make it challenging to estimate drag force. The net force $F_{net(s)}$ can be decomposed using the scalar product into $$F_{ax}(s) = F_{net}(s) \cdot \hat{v}$$

where $\hat{v}$ is the unit vector in the axial direction 302 given by $$\frac{\partial r(s)}{\partial s},$$

and $$F_{rad}(s) = F_{net}(s) - F_{ax}(s)$$

where $F_{ax}(s)$ is the axial force collinear to the lumen centerline and $F_{rad}(s)$ is the radial force perpendicular to the centerline.

The required magnetic force $F_{mag}(s_0)$ to provide an axial force $F_{ax}(s_0)$ at the microrobot location $s_0$ is given by $$F_{mag}(s|_0) = -F_{ax}(s_0) - F_{grav} - F_{buo} - F_{drag}(s_0).$$

Figure 7:
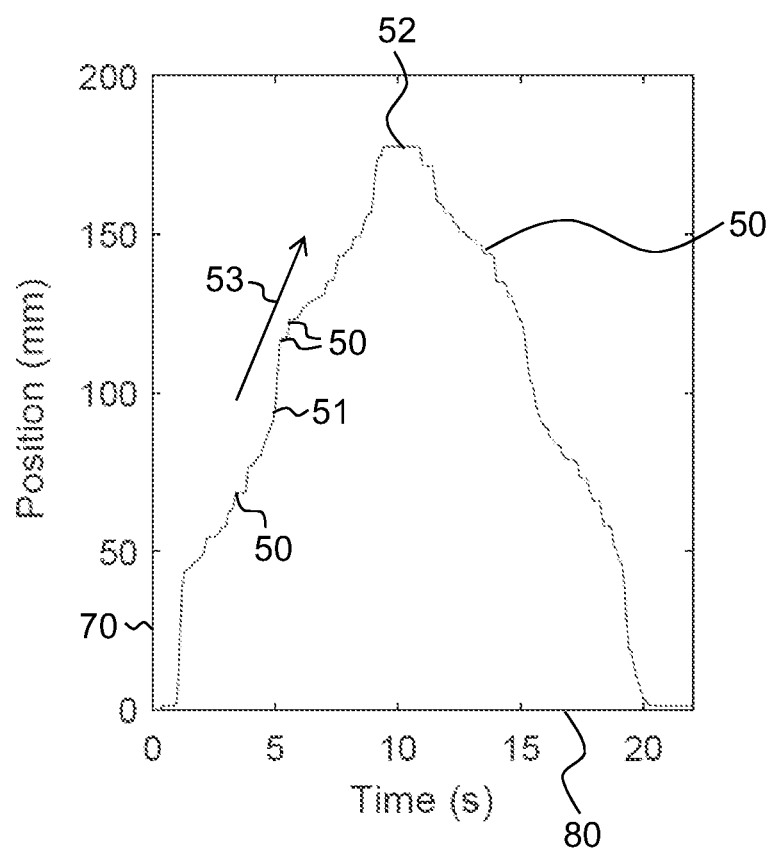
FIG. 7 shows the position against time curve of the movement of the microrobot in the spiral lumen of FIG. 6.

As the microrobot 100 moves along the lumen, the orientation relative to the lumen orientation varies. Therefore, the net force must also have a radial component. The radial force pulls the microrobot against the lumen wall and is balanced with a contact force normal to the wall. Contact with the wall 201 results in a friction force opposing the axial force. Determining when the axial force overcomes friction leads, since static friction is usually higher than kinetic friction, in a stepwise motion (stepwise movement 51 from position 50 to a further position 50 as shown in FIG. 7) and limits precise position control of the microrobot 100. Using a uniform magnetic gradient that creates a magnetic force greater than opposing forces allows navigation of the microrobot 100 along a curved path without knowing the exact magnitude of all the forces or the exact microrobot location.

The limitation of this approach is that stable positions 102 only exist at curved locations along the lumen 205, i.e. the microrobot 101 cannot be controlled along a straight lumen segment 206. This limitation is part of the insight for the present navigation method of using magnetic force inhomogeneity.

One limitation of using the magnetic gradient for microrobot navigation is its rapid decay with distance from the electromagnets. However, by exploiting magnetic gradient inhomogeneity, stable microrobot positions can be realized without relying on lumen curvature for providing stability. Equilibrium positions 102 can be achieved when the net force is equal to zero at the desired target location. Lumen geometry prevents motion in two directions. Therefore, an equilibrium position is stable if motion is prevented along the axial direction. A stable position is present at a location $s_i$ and if $F_{net}(s_i)=0$ and $$\frac{\partial F_{ax}(s_i)}{\partial s} < 0.$$

If the second condition is fulfilled, the microrobot 100 is pulled toward the stable equilibrium position 102. If the axial net force increases along the motion direction, the previously stable equilibrium becomes unstable. With the equilibrium condition, the required magnetic force at a target location is calculated as $$F_{mag}(s_0) = -F_{grav} - F_{buo} - F_{drag}(s_0)$$

The stability criteria is verified, calculating the net force along the path to obtain $$\frac{\partial F_{net}(s)}{\partial s} = \frac{\partial F_{mag}(s)}{\partial s} + \frac{\partial F_{drag}(s)}{\partial s}$$

The derivative of the net force is then decomposed into its radial and axial components. Fiction force has a large effect on microrobot motion toward a stable equilibrium position 102. For small offsets from such a stable equilibrium position 102, net forces are too low to overcome the friction.

Figure 9:
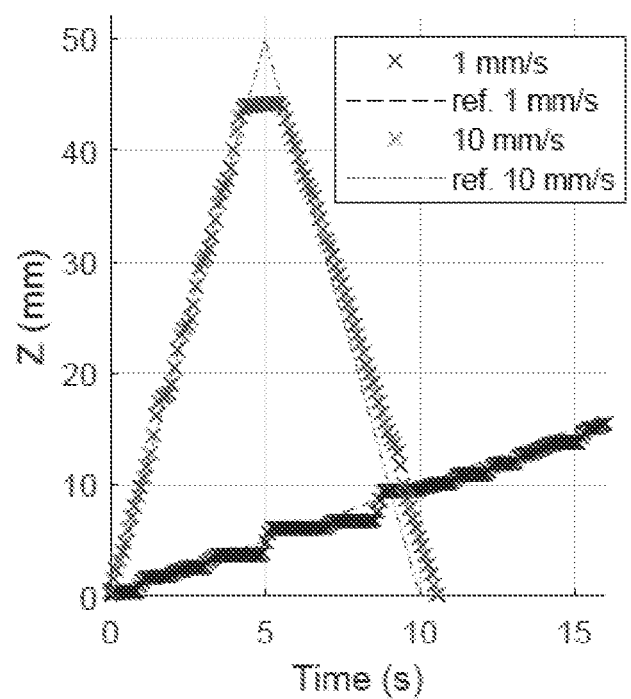
FIG. 9 shows the movement of a microrobot in a straight lumen as represented in FIG. 2.

A spherical microrobot was used to obtain the curves of FIG. 7 and FIG. 9. Such a spherical microrobot aligns with the magnetic field, which results in the dipole moment and the magnetic field having the same orientation.

The magnetic force is dependent on the magnetic gradient and the dipole orientation. Therefore, the control of the magnetic field is crucial even if control of microrobot orientation is not required. For obtaining the results as shown in FIGS. 7 and 9 the magnetic gradient is controlled with a magnetic navigation system with eight electromagnets located around the workspace center. Navigating a spherical hard magnetic microrobot within a magnetic navigation system is an over-actuated system. The number of required controllable electromagnet currents is greater than the three components of the resulting magnetic force. To compute the eight electromagnet currents, a matrix containing the contribution of each electromagnet to the magnetic field and the aligned magnetic gradient is inverted. Then, controlling only the magnetic force requires the selection of an arbitrary magnetic dipole orientation and the corresponding magnetic field orientation.

To obtain a stable equilibrium at a location along the path, the contribution matrix representing the contribution of electromagnet currents to the magnetic field is extended with a row representing the contribution of the electromagnet currents to the aligned magnetic gradient derivative along the lumen axis.

However, linearization at one location for one dipole orientation and one lumen orientation is not sufficient when the direction of the force changes quickly. Therefore, the stability condition is evaluated for a range of axial lumen locations around a target position. To identify which electromagnet current vector to select to move the microrobot to a desired stable position, initially the current vectors are considered that result in zero force on the microrobot 100.

For an arbitrary magnetic field orientation and magnetic field magnitude, $\mathcal{A}$ B,G is decomposed into $\mathcal{A}$ B,G=U$\Sigma$V$^T$, with $$\begin{bmatrix} \mathcal{B}(P) \\ \mathcal{G}(P, M) \end{bmatrix} \begin{bmatrix} i_1 \\ \vdots \\ i_n \end{bmatrix} = \mathcal{A}_{B,G}(P, M) I$$

with $\mathcal{B}$(P) representing the contribution of the electromagnet currents $i_1$ to $i_n$ to the magnetic field and $\mathcal{G}$(P,M) representing the aligned magnetic gradient contribution, using singular value decomposition. V contains the singular current vectors. The seventh and eighth singular current vectors describe the null space. Adding these two current vectors to the current vector computed with $$I = \mathcal{A}_{B,G}(P, M)^\dagger \begin{bmatrix} B_{des} \\ G_{des} \end{bmatrix}$$

where $\dagger$ is related to the pseudoinverse does not change the magnetic force at a particular location along the path. However, this does change the magnetic force around this location. Therefore, an unstable location can become stable. The overall current vector that provides improved stability at a target location can be determined by repeating this for a set of magnetic field orientations.

To estimate the capability of the known 8 magnets magnetic navigation system to navigate a microrobot, an arbitrary magnetic field magnitude of 20 mT, an aligned magnetic gradient magnitude of 0.2 T/m, and ensured that the eight currents were within the linear region of the magnetization curves of all eight electromagnets. The selected magnetic field magnitude is more than sufficient to orient a microrobot 100, and the magnetic gradient results in a magnetic force 150% higher than the gravitational force on a pure NdFeB microrobot. The limit for the linear range is defined by a 10% decrease in the ratio between magnetic field measured and the magnetic field predicted for one electromagnet. The magnetic field orientation and dipole orientation is discretized into 37 azimuthal angles and 37 inclination angles. For each combination the maximum electromagnet current is computed. This results in a four-dimensional array with 37 elements in each dimension. From this multidimensional array, the minimal current required to generate a magnetic in any direction is extracted. Optimal dipole orientations can exhibit discontinuities in terms of magnetic field direction. An alternative is to use a constant dipole orientation with the advantage of keeping the magnetic field orientation constant.

FIG. 6 shows a schematic view of a spiral lumen portion with ten positions of a microrobot 100 at different equilibrium points 102 moved using the method as explained in connection with FIG. 1. A spherical NdFeB magnet with a diameter of 1 mm is inserted into a transparent lumen with an internal diameter of 2 mm and a length of 180 mm. The lumen is shaped into a spiral 210 with a geometry similar to the cochlea spiral and positioned inside the magnetic navigation system in a vertical plane. The lumen is filled with low-viscosity air, making the navigation problem more challenging. The magnetic force must be sufficiently high to compensate gravity (i.e. for NdFeB a magnetic gradient of 0.08 T/m is required). The magnetic gradient is then used to move the microrobot from one spiral extremity to the next extremity by rotating the magnetic gradient and maintaining a fixed dipole orientation. The microrobot 100 moves from proximal to distal ends in ten seconds. The composite image represents the microrobot 100 at each second during the forward motion, and the graph shows the position along the lumen during forward and backward motion. Once the microrobot 100 has reached the distal end of the 180 mm lumen, the direction is inverted to retrieve the microrobot 100 at the proximal end.

For different magnetic field magnitudes, gradient magnitudes, and gradient rotation speeds, the microrobot's ability to move from the proximal extremity of the spiral to the distal extremity and then back were evaluated. The tests were successful for magnetic field magnitudes of 5 mT, 10 mT and 20 mT. Achieving a positive result for a magnetic field magnitude of 2.5 mT was more challenging. This is expected as the larger magnetic gradient required for a field magnitude of 2.5 mT resulted in a faster change in the magnetic field direction. Precisely controlling a microrobot 100 with a low magnetic field magnitude requires position feedback and an extremely precise magnetic field model.

There is a coupling between the gradient magnitude and the maximum gradient rotation frequency. With a gradient magnitude of 0.2 T/m, moving in the spiral was successful with a rotation period as low as 4 s. With a gradient magnitude of 0.15 T/m the task required a period of at least 8 s.

The task of navigating the microrobot 100 in a two-and-a half turn spiral forward and backward is achieved in twenty seconds with a total travel distance of 360 mm. Similar results can be expected for this microrobot size inside a liquid with low viscosity, i.e. below 10 cP, because the main limiting factor is the slow dynamics of the human scale magnetic navigation system. These slow dynamics are a result of unavoidable magnetic induction in the electromagnets.

Here, FIG. 6 shows a sequence of stable positions 102 which can be achieved by running the method of FIG. 10 where one time the preoperative imaging 110 is obtained and then the control unit 112 achieves a sequence of microrobot stable positions 118 through generating (114) a net field of force 116 to move the microrobot. It is also possible that the different stable positions 118 as shown in FIG. 6 are controlled through operative imaging 120 and provide input to the control unit 112 to adapt the movement to the next intended and calculated stable position 118.

In order to show magnetic gradient control with junctions or bifurcations, a labyrinth with dimensions 60 mm by 60 mm was used in which the metal bead is replaced with a magnetic bead (NdFeB) with a diameter of 3 mm. Then bifurcations 202 are present like in the Circle of Willis, i.e. a circulatory anastomose in the brain as shown in FIG. 8. A large magnetic bead is selected to facilitate visualization. The same result can be obtained with a 1 mm diameter magnetic bead. The magnetic force direction and magnitude at the center of the workspace was controlled remotely by a user with visual feedback. Navigation between two faces of the labyrinth from a start position to a goal position was executed a number of times with a mean execution time of 109s and a standard deviation of 30s. It was possible to accomplish the navigation by varying the orientation of the magnetic force. Some challenging junctions required that the magnetic gradient magnitude is varied to obtain different dynamic trajectories of the bead and create additional stable positions using magnetic gradient inhomogeneity. The execution speed is primarily limited by the user who decides the direction of the next motion and then inputs the command to the system. Improvements in term of user interface, user training, and task automation can significantly reduce the above-mentioned execution time. Despite the complex path with a large number of junctions and linear segments, the navigation of the magnet did not present major challenges. This demonstrates the potential to navigate inside complex geometries such as of the Circle of Willis as shown in FIG. 8.

Finally, FIG. 9 shows the movement of a microrobot in a straight lumen 206 as in FIG. 2. The magnetic gradient control in a straight lumen uses magnetic gradient inhomogeneity, wherein a 1 mm microrobot 100 is inserted into a vertical lumen with an internal diameter of 2 mm and with magnetic force decreasing in the vertical direction. By changing the profile of the magnetic force, the microrobot moves to different locations along the lumen. All tests were performed open-loop, and evaluation of the results was limited to the relative motion of the microrobot. To evaluate absolute position accuracy requires implementation of closed-loop control to correct errors in the microrobot parameters, magnetic navigation system calibration, and position registration of the different system (e.g. camera, x-ray, lumen geometry, magnetic navigation system). Therefore, relative motion is the preferred metric to evaluate navigation capabilities as the relative motion is less dependent on offset errors or control parameters and is the manner in which the system will be used clinically.

FIG. 9 shows a microrobot being moved inside a straight vertical lumen by translating the stable equilibrium location along the lumen. The microrobot vertical position is represented when moving the stable equilibrium location vertically with a speed of 1 mm/s and 10 mm/s. In both cases the microrobot robot moves at the desired speed.

In a first experiment, the stable equilibrium point is moved in the vertical direction with a speed of 1 mm/s. The microrobot follows a vertical path with an average step size of less than 1 mm. These steps were empirically selected based on friction between the microrobot and the lumen and did not require significant tuning.

In a second experiment, the static equilibrium point is moved in the vertical direction with a speed of 10 mm/s forward and backward. This experiment is repeated with a net force pulling the microrobot to the left, to the front, and to the right of the lumen. The net force pulling the microrobot toward the corresponding lumen wall is shown for each experiment. The microrobot stops for 1s when the motion direction is reversed. The damping of the motion is due to friction and the limited dynamics of the magnetic navigation system which does not reach a steady state before the motion direction is reversed.

Figure 12:
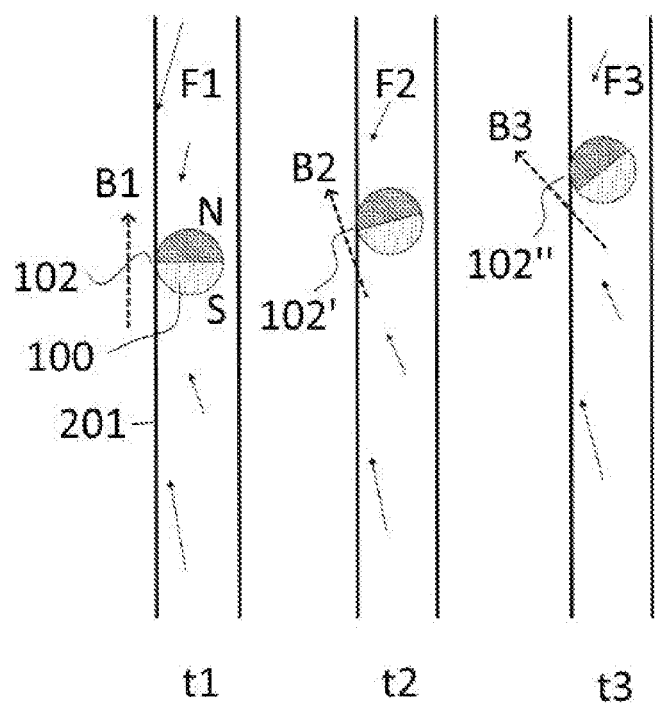

FIG. 12 shows a schematic cross section view of a straight lumen portion at three successive times t1, t2 and t3 corresponding to three successive field generating steps, wherein each time the microrobot 100 is stabilized at a different equilibrium position against the wall 201, illustrated by reference 102 at t1, 102' at t2 and 102" at t3, on the wall 201 of the lumen under the action of the net field of force F1 at t1, F2 at t2 and F3 at t3. In the present embodiment, the microrobot 100 has a circular cross section at least in the plane of the cross section and can be of an essentially spherical or cylindrical form. The microrobot 100 includes a magnetic material forming a magnet with a north magnetic pole N and south magnetic pole S, each illustrated schematically as shaded halves of the cross section.

At t1, the magnetic field B1 is directed in the direction represented by the dotted arrow B1, presently essentially parallel to the straight lumen portion for the sake of simplicity only, and the magnet has its north and south poles aligned with the magnetic field B1. The net field of force F1 represented by the arrows in the lumen is the sum of all the forces acting on the microrobot, including the magnetic field of force related to the magnetic field B1, the gravity field of force, the buoyancy force and additional forces acting on the microrobot.

In the field generating step implemented after t1, the direction of the magnetic field B1 is changed, presently after a counterclockwise rotation, to the direction B2 and the microrobot 100 rotates counterclockwise under the action of the torque acting on the microrobot to align its north and south poles with the direction of the magnetic field B2. Under the action of the net field of force F2 represented by the arrows in the lumen, the microrobot 100 moves to and is kept at the new equilibrium position 102' against the wall 201. In the present case, the displacement of the microrobot 100 corresponds to the combination of the rotation due to the change of direction of the magnetic field B1 and a translation along the wall 201 under the action of the net field of force F2.

In the field generating step implemented after t2, the direction of the magnetic field B2 is changed, presently after a further counterclockwise rotation, to the direction B3 and the microrobot 100 rotates counterclockwise under the action of the torque acting on the microrobot to align its north and south poles with the direction of the magnetic field B3. Under the action of the net field of force F3 represented by the arrows in the lumen, the microrobot 100 moves to and is kept at the new equilibrium position 102" against the wall 201.

LIST OF REFERENCE SIGNS

| 50 | stop at equilibrium point |
| 51 | movement between equilibrium points |
| 52 | innermost point of travel |
| 53 | displacement |
| 70 | position (from starting point) |
| 80 | time (after start) |
| 100 | microrobot |
| 101 | microrobot at non equilibrium point |
| 102 | microrobot at equilibrium point |
| 110 | preoperative imaging |
| 112 | control unit |
| 114 | field of force generator |
| 116 | field of force |
| 118 | micro robot stable position |
| 120 | operative imaging |
| 200 | space |
| 201 | wall |
| 202 | bifurcation |
| 205 | curved lumen portion |
| 206 | straight lumen portion |
| 207 | flat wall |
| 208 | side open straight lumen portion |
| 209 | dish like space portion |
| 210 | hollow spiral |
| 220 | Circle of Willis |
| 300 | field of force |
| 301 | force value |
| 302 | direction of the net force |

The invention claimed is:

1. A microrobot system, comprising:
a microrobot for displacement through a space having a wall, the microrobot being formed with a body containing a magnetic field of force responsive material, wherein, in response to a magnetic field of force, a force is applied to the microrobot in a direction of the magnetic field of force;
a magnetic field of force generator configured to generate the magnetic field of force such that the magnetic field of force has a predetermined direction, amplitude and spatial variation for application to the microrobot to propel the microrobot through the space in a direction of a net field of force; and
a control unit connected to the magnetic field of force generator, said control unit being configured to calculate the direction, an amplitude, and a spatial variation of the net field of force acting on the microrobot, to control a displacement of the microrobot through the space and against the wall and to calculate an equilibrium point of the microrobot on the wall using data relating to an image of the space and the calculated direction, amplitude, and spatial variation of the net field of force, and to create a sequence of field generating steps executed one after the other, wherein
at the equilibrium point, a sum of all forces parallel to a plane tangent to the equilibrium point is cancelled and a normal force applied at the equilibrium point on the microrobot is cancelled by a surface contact force, and
each field generating step comprises providing the direction, the amplitude and the spatial variation of the net field of force for the displacement of the microrobot in the space and against the wall from a starting equilibrium point on the wall to another equilibrium point on the wall.

2. The microrobot system according to claim 1, wherein the magnetic field of force generator comprises a set of electromagnets.

3. The microrobot system according to claim 2, wherein the magnetic field of force generator comprises a magnetic resonance imaging system.

4. The microrobot system according to claim 1, wherein the magnetic field of force generator comprises a set of movable permanent magnets.

5. The microrobot system according to claim 1, wherein the microrobot is spheroidal.

6. The microrobot system according to claim 1, wherein the control unit is configured to execute the field generating steps at a frequency ranging from 0.2 Hz to 1000 Hz.

7. The microrobot system according to claim 1, wherein the control unit is configured to trigger the magnetic field of force generator to change the direction of the magnetic field in at least one field of force generating step.

8. The microrobot system according to claim 1, wherein the data relating to the image of the space are generated prior to an introduction of the microrobot into the space.

9. The microrobot system according to claim 1, wherein the data relating to the image of the space are generated for a local environment of the microrobot in real-time.

10. The microrobot system according to claim 1, wherein the control unit is configured to calculate the direction, the amplitude, and the spatial variation of the magnetic field of force prior to a predetermined number of all of the field generating steps of the sequence, or prior to all of the field generating steps.

11. The control unit for use in of the microrobot system according to claim 1, the control unit comprising a processor configured to carry out the steps of:
    obtaining the data relating to the image of the space having the wall from an imaging system;
    determining a first position of the microrobot in the space;
    calculating the direction, the amplitude, and the spatial variation of the net field of force applied on the microrobot corresponding to the direction, the amplitude, and the spatial variation of the magnetic field of force in the space;
    calculating the displacement of the microrobot through the space and against the wall, using the calculated direction, amplitude, and spatial variation of the net field of force and the data relating to the image of the space, from the first position to a second position of the microrobot on the wall under the net field of force;
    repeating the calculation for different magnetic fields of force in the space;
    selecting the magnetic field of force corresponding to an equilibrium position of the microrobot on the wall which can be used as the second position; and
    transferring the direction, the amplitude, and the spatial variation of the selected magnetic field of force in the space corresponding to the equilibrium point for the second position to the magnetic field of force generator configured to generate the magnetic field of force, and propelling the microrobot through the space in the direction of the net field of force from the first position to the second position.

12. The control unit according to claim 11, wherein the processor is configured to carry out the step of calculating a change of direction of the magnetic field necessary to rotate the microrobot.

13. A non-transitory computer readable medium storing thereon a program comprising instructions which, when the instructions are executed by the processor of the control unit claimed in claim 11, cause the processor to carry out the steps of:
    determining the first position of the microrobot in the space;
    calculating the direction, the amplitude, and the spatial variation of the net field of force applied on the microrobot corresponding to the direction, the amplitude, and the spatial variation of the magnetic field of force in the space;
    calculating the displacement of the microrobot through the space and against the wall, using the calculated direction, amplitude, and spatial variation of the net field of force and the data relating to the image of the space, from the first position to the second position of the microrobot on the wall under the net field of force;
    repeating the calculation for the different magnetic fields of force in the space;
    selecting the magnetic field of force corresponding to the equilibrium position of the microrobot on the wall which can be used as the second position; and
    transferring the direction, the amplitude, and the spatial variation of the selected magnetic field of force in the space corresponding to the equilibrium point for the second position to the magnetic field of force generator configured to generate the magnetic field of force, and propelling the microrobot through the space in the direction of the net field of force from the first position to the second position.

14. A method for propelling and controlling displacement of a microrobot in a space having a wall, comprising the steps of:
    forming the microrobot with a body containing a magnetic field of force responsive material, wherein a force is applied to the microrobot in response to a magnetic field of force in a direction of the magnetic field of force;
    positioning the microrobot in the space for displacement in that space; and
    generating the magnetic field of force with a predetermined spatial variation and applying the magnetic field of force to the microrobot to propel the microrobot through the space in a direction of a net field of force, wherein
    a sequence of field generating steps are provided, executed one after the other, wherein each field generating step comprises the step of providing the direction, an amplitude, and a spatial variation of the net field of force to control the displacement of the microrobot in the space and against the wall from a starting equilibrium point to another equilibrium point, and
    at each equilibrium point, a sum of all forces parallel to a plane tangent to the equilibrium point is cancelled and a normal force applied at the equilibrium point on the microrobot is cancelled by a surface contact force.

15. The method according to claim 14, wherein a subsequent field generating step is engaged when the other equilibrium point of a current field generating step is reached.

16. The method according to claim 14, wherein the step of providing the direction, the amplitude, and the spatial variation of the net field of force to control the displacement of the microrobot is performed for a predetermined number of all of the field generating steps of the sequence or for all of the field generating steps, prior to the execution of the predetermined number of all of the field generating steps or of all of the field generating steps, respectively.

17. The method according to claim 14, wherein the step of providing the direction, the amplitude, and the spatial variation of the net field of force to control the displacement of the microrobot for a specific field generating step comprises calculating said direction, said amplitude, and said spatial variation of the magnetic field of force at the beginning of said field generating step.

* * * * *